(12) United States Patent
Choi et al.

(10) Patent No.: US 9,850,259 B2
(45) Date of Patent: Dec. 26, 2017

(54) APPARATUS FOR PURIFYING ORGANIC COMPOUND AND METHOD OF PURIFYING ORGANIC COMPOUND

(71) Applicants: Sang June Choi, Uiwang-si (KR); Hyeong Guk Yoo, Uiwang-si (KR); Hee Jun Jeong, Uiwang-si (KR); Myeong Soon Kang, Uiwang-si (KR); Hae Sang Yoon, Uiwang-si (KR)

(72) Inventors: Sang June Choi, Uiwang-si (KR); Hyeong Guk Yoo, Uiwang-si (KR); Hee Jun Jeong, Uiwang-si (KR); Myeong Soon Kang, Uiwang-si (KR); Hae Sang Yoon, Uiwang-si (KR)

(73) Assignee: CHEIL INDUSTRIES, INC., Gumi-Si, Kyeongsangbuk-Do (KR)

( * ) Notice: Subject to any disclaimer, the term of this patent is extended or adjusted under 35 U.S.C. 154(b) by 870 days.

(21) Appl. No.: 14/259,719

(22) Filed: Apr. 23, 2014

(65) Prior Publication Data

US 2014/0336384 A1    Nov. 13, 2014

(30) Foreign Application Priority Data

May 13, 2013 (KR) .......................... 10-2013-0054062

(51) Int. Cl.
   *B01J 19/00*    (2006.01)
   *C07F 5/06*    (2006.01)
   (Continued)

(52) U.S. Cl.
   CPC .............. *C07F 5/069* (2013.01); *B01D 1/223* (2013.01); *B01D 1/225* (2013.01); *B01D 1/226* (2013.01); *B01D 1/228* (2013.01); *B01D 7/02* (2013.01)

(58) Field of Classification Search
   CPC .................................. B01D 7/00; C07F 5/069
   (Continued)

(56) References Cited

U.S. PATENT DOCUMENTS 1,445,870 A    2/1923    Cole
2,628,892 A    2/1953    Reid
(Continued)

FOREIGN PATENT DOCUMENTS

CN    2168632 Y    6/1994
CN    2668212 Y    1/2005
(Continued)

OTHER PUBLICATIONS

English Translation of Japanese Document No. JP 09295949A provided by European Patent Office Patent Translate: Maruyama, Purifier Apparatus for e.g. organic liquid crystal compounds where temperatures of first and second spherical vessels can be adjusted independently by heaters, Nov. 18, 1997.*

(Continued)

*Primary Examiner* — Kevin Joyner
(74) *Attorney, Agent, or Firm* — Lee & Morse, P.C.

(57) ABSTRACT

An apparatus for purifying an organic compound and a method of purifying an organic compound, the apparatus including an inner tube that receives a purification target material therein; a heater that heats the purification target material received in the inner tube; an evacuator that evacuates the inner tube into a vacuum; and a driving device that drives the inner tube.

20 Claims, 7 Drawing Sheets

(51) Int. Cl.
*B01D 1/22* (2006.01)
*B01D 7/02* (2006.01)
(58) Field of Classification Search
USPC .......................................................... 422/198
See application file for complete search history.

(56) References Cited

U.S. PATENT DOCUMENTS 3,034,573 A   5/1962  Ueberwasser et al.
3,840,349 A  10/1974  McGhie

FOREIGN PATENT DOCUMENTS

| CN | 1714061 A      | 12/2005  |
| FR | 2704446        | 11/1994  |
| GB | 509242 A       | 7/1939   |
| JP | 09295949 A   * | 11/1997  |
| KR | 10-0497448 B1  | 7/2005   |

OTHER PUBLICATIONS

Office Action dated Jul. 15, 2015 in corresponding Chinese Patent Application No. 20141018072.2.
Search Report dated Sep. 25, 2014 in corresponding European Patent Application No. 14166693.3.
Chinese Office Action dated Mar. 17, 2016 in Corresponding Chinese Patent Application No. 201410182072.2.

\* cited by examiner

APPARATUS FOR PURIFYING ORGANIC COMPOUND AND METHOD OF PURIFYING ORGANIC COMPOUND

CROSS-REFERENCE TO RELATED APPLICATION

Korean Patent Application No. 10-2013-0054062, filed on May 13, 2013, in the Korean Intellectual Property Office, and entitled: "Apparatus For Purifying Organicelectroluminescent Material And Method For Purifying Organic Compound," is incorporated by reference herein in its entirety.

BACKGROUND

1. Field

Embodiments relate to an apparatus for purifying an organic compound and a method of purifying an organic compound.

2. Description of the Related Art

An organic electroluminescent device emits light through recombination of electrons and holes in an organic film between an electron injection electrode (e.g., a negative electrode) and a hole injection electrode (e.g., a positive electrode) when electric charges are injected into the organic film, and has characteristics, such as low voltage operation, low power consumption, and the like.

The organic electroluminescent device may be a flat panel display based on a phenomenon wherein light is emitted through conversion of electric energy into light energy when direct current (DC) voltage is applied to a stacked layer of organic materials.

SUMMARY

Embodiments are directed to an apparatus for purifying an organic compound and a method of purifying an organic compound.

The embodiments may be realized by providing an apparatus for purifying an organic compound, the apparatus including an inner tube that receives a purification target material therein; a heater that heats the purification target material received in the inner tube; an evacuator that evacuates the inner tube into a vacuum; and a driving device that drives the inner tube.

The inner tube may include a supply unit to which the purification target material is supplied; and a collecting unit in which the purification target material is sublimated or liquefied as it moves toward the evacuator.

At least one collecting unit may be between the supply unit and the evacuator.

The apparatus may further include a buffer between the supply unit and the collecting unit, the buffer collecting foreign matter from the purification target material that is sublimated or evaporated in the supply unit.

The supply unit may include a deposition portion that stores the purification target material, the deposition portion having an inner wall on which the purification target material is deposited as a thin film, and a discharge port open toward the collecting unit, the discharge port being configured to discharge the sublimated or evaporated purification target material from the deposition portion toward the collecting unit; wherein the discharge port is concentric with the deposition portion, the discharge port having a diameter smaller than a diameter of the deposition portion.

The driving device may include a drive unit that generates power; and a power transmission unit that transmits the power generated by the drive unit to the supply unit to move the supply unit.

The power transmission unit may rotate the supply unit.

The power transmission unit may include a power transmission member that receives power from the drive unit; and a supply unit-holding member that transmits power received in cooperation with the power transmission member to the supply unit.

The supply unit-holding member may include an outward holding portion that extends to surround an outer surface of the supply unit; and a longitudinal holding portion that extends in a longitudinal direction of the supply unit and intersects the outward holding portion.

The apparatus may further include a mounting portion on at least one of the outward holding portion and the longitudinal holding portion; a pressing portion on the mounting portion, the pressing portion supporting the supply unit; and a resilient portion that presses the pressing portion toward the supply unit.

The supply unit-holding member may be separated from the supply unit, the mounting portion may include a through hole penetrating the supply unit-holding member further, and the pressing portion may contact the supply unit.

The supply unit may be detachably coupled with the power transmission unit.

The heater may heat the purification target material that is in the supply unit to be sublimated or evaporated, and may heat the purification target material that is moving along the collecting unit to be sublimated or liquefied.

The heater may include a supply unit-heating portion that heats the supply unit; and a collecting unit-heating portion that heats the collecting unit, the collecting unit-heating portion heating the collecting unit to a temperature that is lower than a temperature to which the supply unit-heating portion heats the supply unit.

The inner tube may be divided into a plurality of heating zones that are arranged from the driving device to the evacuator, and the heater may heat the inner tube such that a zone closest to the driving device has a highest temperature.

The apparatus may further include an outer tube accommodating the inner tube, the driving device being at one side of the outer tube and at the evacuator being at another side of the outer tube; and a sealing portion that seals a coupling portion between the driving device and the outer tube to seal the outer tube.

The apparatus may further include a carrying gas supplier that supplies a carrying gas, the carrying gas moving the sublimated or evaporated purification target material toward the evacuator.

The inner tube may include a surface-area enlarging portion that enlarges a surface area inside the inner tube.

The organic compound may include a material for an organic electroluminescent device.

The embodiments may be realized by providing a method of purifying an organic compound, the method including supplying a purification target material to a supply unit; melting the purification target material; rotating the supply unit to form a thin film of the purification target material on an inner wall of the supply unit; heating the purification target material in the supply unit to be sublimated or evaporated; and purifying the purification target material by sublimating or liquefying the purification target material while moving the purification target material toward an evacuator.

Supplying the purification target material may include inserting the supply unit into an outer tube and then blocking the supply unit from external air with a sealing portion.

Heating the purification target material may include heating the inner tube that is divided into a plurality of zones such that a zone farthest away from the evacuator has a temperature equal to or higher than a sublimation or evaporation point of the purification target material, and other zones have a temperature lower than the sublimation or evaporation point of the purification target material.

Heating the purification target material may include heating the plurality of zones to have different temperatures such that a temperature gradient is formed along the inner tube.

Rotating the supply unit may include rotating the supply unit after completely melting the purification target material.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
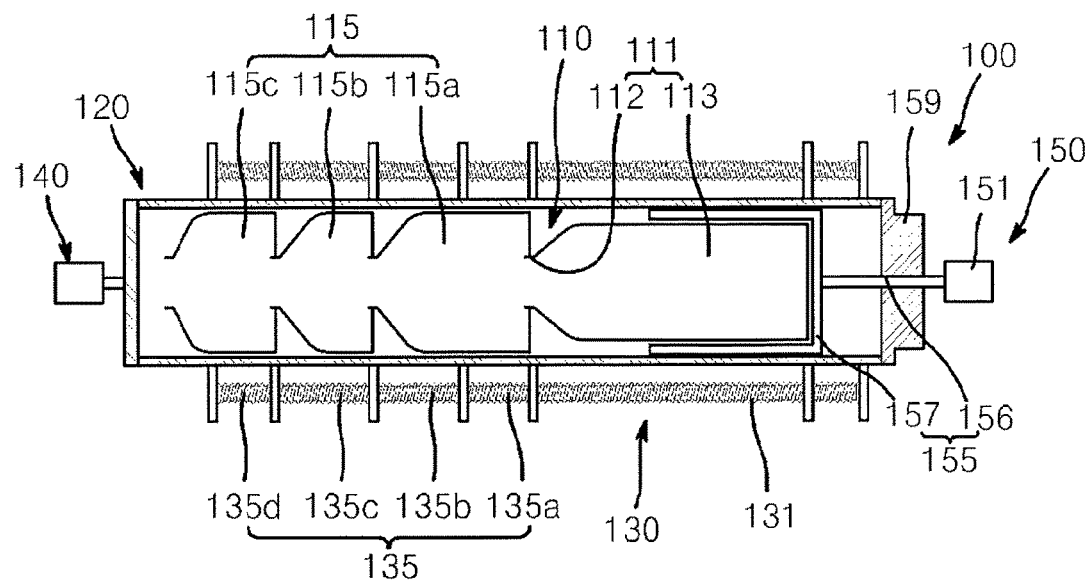
FIG. 1 illustrates a schematic view of an apparatus for purifying an organic compound in accordance with a first embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

Furthermore, the terms used herein are defined by taking functions of the embodiments into account and can be changed according to user or operator's custom or intention. Therefore, definition of the terms should be made according to the overall disclosure set forth herein.

In a first embodiment, a purification target material P may include, e.g., an organic compound. In an implementation, the organic compound may include, e.g., a material for organic optoelectric devices. For example, the organic compound may include not only a pure organic compound but also a composite organic/inorganic compound, such as an organometallic complex compound, and/or impurities. For example, the organic compound according to an embodiment may include organic compounds for medicines, organic compounds for electronic materials, and/or organic compounds for chemical materials.

The organic optoelectric device may convert electric energy into light energy, or vice versa. The organic optoelectric device may refer to a device in which electric charges are exchanged between an electrode and an organic material using holes or electrons. The organic optoelectric device may be broadly classified into two types in accordance with operation. One type may include an electronic device in which an exciton is generated in an organic layer by a photon introduced from an external light source into the device and is divided into an electron and a hole, which in turn are transported to different electrodes to be used as a current source. Another type may include an electronic device in which voltage or current is deposited to two or more electrodes so as to inject holes or electrons into an organic semiconductor forming an interface with the electrodes, and which is operated by the injected electrons and holes.

Examples of the organic optoelectric device may include an organic electroluminescent device, an organic light emitting device, an organic solar cell, an organic photo conductor drum, an organic transistor, and the like, all of which include a hole injection or transport material, an electron injection or transport material, or a light emitting material to drive the device.

A material for the organic optoelectric device (according to a first embodiment) may include a material for an organic light emitting diode (OLED). Among materials for the organic light emitting diode, examples of organic compounds (e.g., a composite organic/inorganic compound, such as an organic metal composite compound) may include organic compounds for a dopant, a host, an auxiliary hole transport layer, a hole transport layer, a hole injection layer, an electron injection layer, an auxiliary electron transport layer, an electron transport layer, or the like. A purification target material according to an embodiment may be one thereamong.

Examples of the material that may be used to form the electron transport layer may include quinoline, 2-(4-biphenylyl)-5-(4-t-butylphenyl)-1,3,4-oxadiazole (PBD), 4,7-diphenyl-1,10-phenanthroline (Bphen), tris(8-hydroxyquinoline)aluminum (Alq3), beryllium bis(benzoquinolin-10-olate) (Bebq2), etc.

Figure 2:
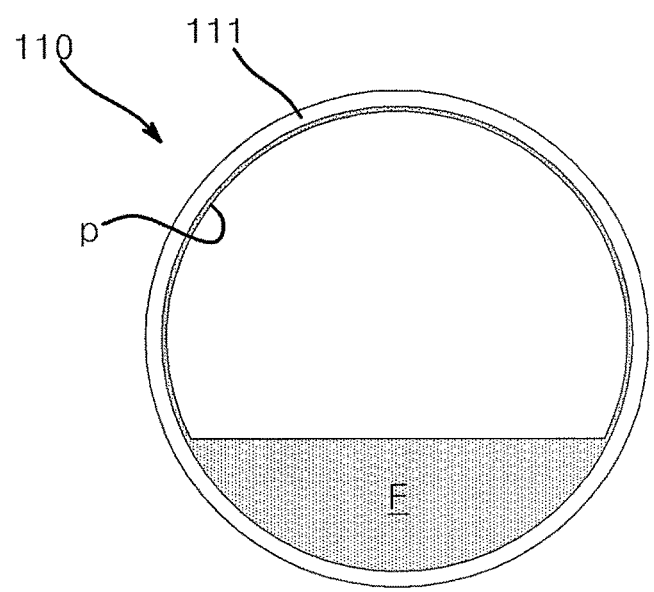
FIG. 2 illustrates a sectional view of a deposition portion of the apparatus in accordance with the first embodiment, showing a deposited state of a thin film thereon.
Figure 3:
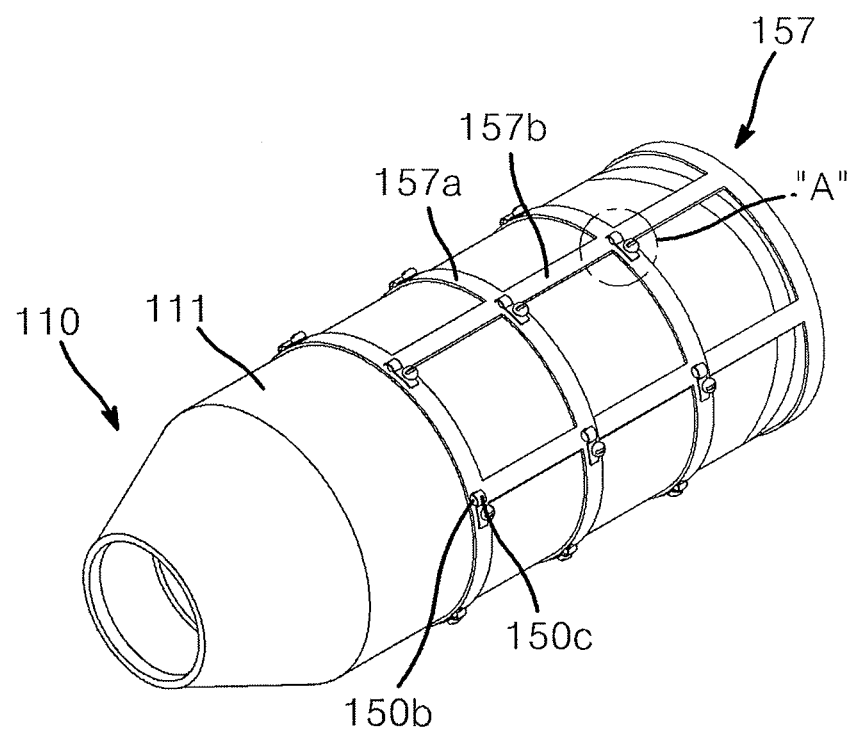
FIG. 3 illustrates a perspective view showing coupling between a supply unit and a power transmission unit of the apparatus in accordance with the first embodiment.
Figure 4:
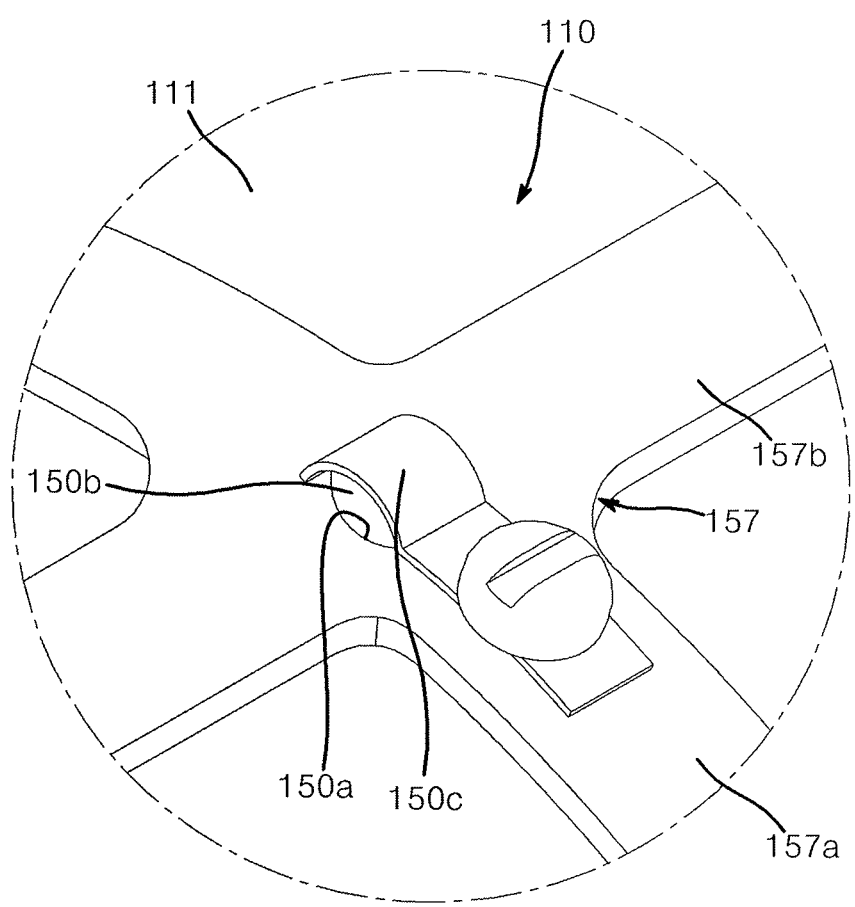
FIG. 4 illustrates an enlarged view of Part A in FIG. 3.
Figure 5:
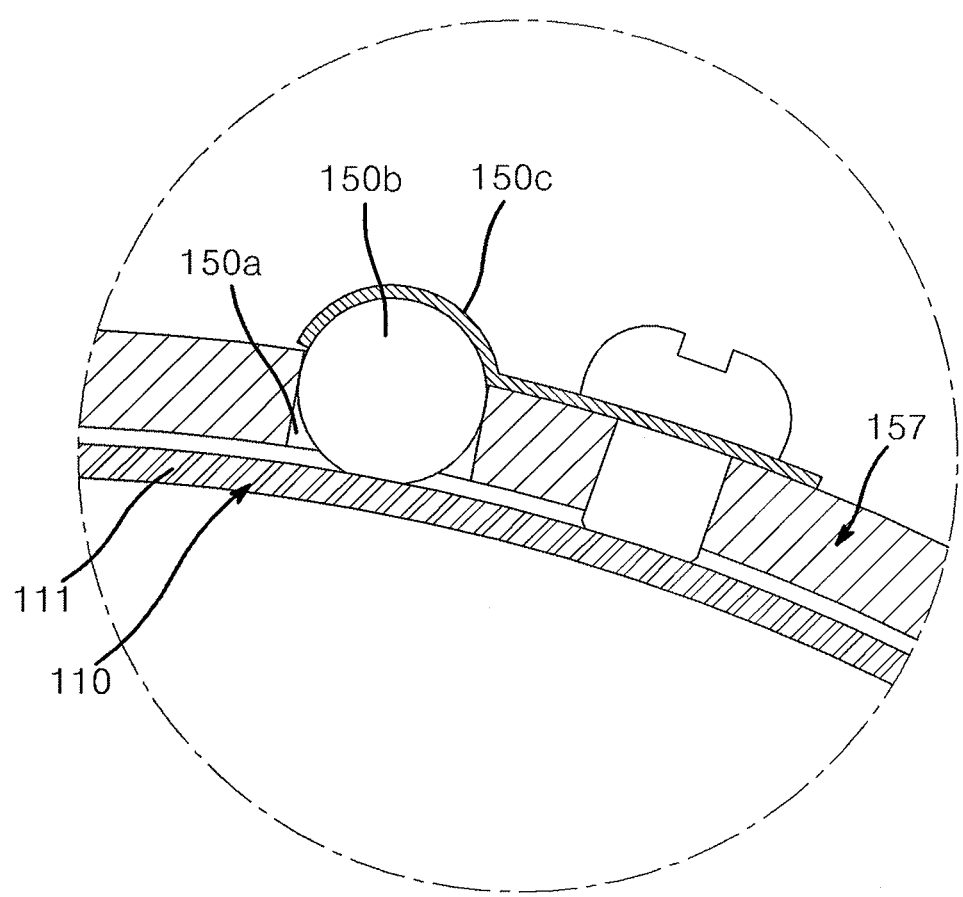
FIG. 5 illustrates a sectional view of Part A in FIG. 3.

FIG. 1 illustrates a schematic view of an apparatus for purifying an organic compound in accordance with a first embodiment. FIG. 2 illustrates a sectional view of a deposition portion of the apparatus in accordance with the first embodiment, showing a deposited state of a thin film thereon. FIG. 3 illustrates a perspective view showing coupling between a supply unit and a power transmission unit of the apparatus in accordance with the first embodiment. FIG. 4 illustrates an enlarged view of Part A in FIG. 3, and FIG. 5 illustrates a sectional view of Part A in FIG. 3.

Referring to FIG. 1, an apparatus 100 for purifying an organic compound according to a first embodiment may include an inner tube 110, an outer tube 120, a heater 130, an evacuator 140, and a driving device 150.

The inner tube 110 may receive and/or accommodate a purification target material. In this embodiment, the inner tube 110 may be rotatable and may receive the purification target material therein. The inner tube 110 may include a supply unit 111 and a collecting unit 115.

The purification target material may be supplied to the supply unit 111. The supply unit 111 may correspond to or may be a section of the inner tube 110 that is closest to the driving device 150 (described below), and may include a discharge port 112 and a deposition portion 113.

In an implementation, the supply unit 111 may be formed of quartz and may have a circular tube shape, which is open at one side thereof (e.g., at the discharge port 112) and is closed at the other side thereof. The discharge port 112 may be open toward the collecting unit 115 at one side of the supply unit 111 such that the supply unit 111 is open toward the collecting unit 115 (described below).

Referring to FIGS. 1 and 2, the deposition portion 113 may correspond to or may be a portion of the supply unit 111 that has a cylindrical shape. The deposition portion 113 may store the purification target material therein (e.g., initially store), and the purification target material stored in the deposition portion 113 may be heated and melted in the deposition portion 113. The purification target material (that is melted in the deposition portion 113) may be deposited as a thin film on an inner wall of the deposition portion 113 and may be sublimated or evaporated upon operation of the supply unit 111, e.g., upon rotation (and heating) of the supply unit 111.

In an implementation, the melted purification target material F may be deposited as a thin film p over or on an inner wall of the deposition portion 113, as the supply unit 111 is rotated by the driving device 150 with the purification target material melted in the deposition portion 113. The thin film p of the purification target material on the inner wall of the deposition portion 113 may enlarge a surface area through which the purification target material is sublimated or evaporated. Accordingly, the purification target material may be relatively quickly and efficiently sublimated or evaporated at the same temperature.

In the deposition portion 113, the sublimated or evaporated purification target material may be discharged toward the collecting unit 115 through the discharge port 112. The discharge port 112 (through which the sublimated or evaporated purification target material is discharged) may have a height that is greater than a height of the deposition portion 113. For example, a distance from an outer side of the apparatus 100 to an inner surface of the discharge port 112 may be greater than a distance from the outer side of the apparatus 100 to the inner wall of the deposition portion. For example, the discharge port 112 may be concentric with the deposition portion 113, and a diameter of the discharge port 112 may be smaller than a diameter of the deposition portion 113. According to the present embodiment, the supply unit 111 may rotate, and the discharge port 112 may have the greater height (e.g., smaller diameter) than the deposition portion 113 to help prevent the purification target material F (e.g., initially stored and melted in the deposition portion 113) from running over to an outside of the supply unit 111 during rotation of the supply unit 111.

In the collecting unit 115, the purification target material may be sublimated or liquefied (e.g., melted) while moving toward the evacuator 140. The collecting unit 115 may be between the supply unit 111 and the evacuator 140. In an implementation, at least one collecting unit 115 may be between the supply unit 111 and the evacuator 140.

In an implementation, three collecting units 115a, 115b, 115c may be between the supply unit 111 and the evacuator 140. In an implementation, the purification target material having the highest purity may be sublimated or liquefied or may be collected in a first collecting unit 115a (closest to the supply unit 111), and the purification target material having the lowest purity and more foreign matter may be sublimated or liquefied or may be collected in a third collecting unit 115c (closest to the evacuator 140). In an implementation, the purification target material having the same purity as that in the first collecting unit 115a, and/or containing more foreign matter, may be sublimated or liquefied or may be collected in a second collecting unit 115b that is between the first collecting unit 115a and the third collecting unit 115c.

In an implementation, the three collecting units 115a, 115b, 115c may be between the supply unit 111 and the evacuator 140. In an implementation, one or two collecting units 115, or four or more collecting units 115, may be disposed therebetween, and various modifications can be made according to desired properties, heating temperature, and/or pressure of the purification target material.

The outer tube 120 may be disposed outside of the inner tube 110. For example, the inner tube 110 may be accommodated in the outer tube 120. The driving device 150 may be provided at one side of the outer tube 120, and the evacuator 140 may be provided at another side of the outer tube 120.

The heater 130 may heat the purification target material in the inner tube 110. For example, the heater 130 may heat the purification target material in the supply unit 111 to sublimate or evaporate the purification target material. The heater 130 may also heat the purification target material that is moving along the collecting unit 115 to sublimate or liquefy the purification target material.

In an implementation, the heater 130 may include a supply unit-heating portion 131 and a collecting unit-heating portion 135. The supply unit-heating portion 131 may be disposed at a side of the apparatus 100 corresponding to the supply unit 111, and may heat the supply unit 111 such that the purification target material in the supply unit 111 may be sublimated or evaporated. The collecting unit-heating portion 135 may be disposed at a side of the apparatus 100 corresponding with the collecting unit 115, and may heat the collecting unit 115 such that the collecting unit 115 has a temperature lower than the supply unit-heating portion 131, thereby heating the purification target material moving along the collecting unit 115 to be sublimated or liquefied in the collecting unit 115.

In an implementation, the inner tube 110 may be divided into a plurality of zones to be heated, e.g., from the driving device 150 toward the evacuator 140. In an implementation, the heater 130 may heat the inner tube 110 such that a zone closest to the driving device 150 has the highest temperature. With this structure, the inner tube 110 may be heated in a state of being divided into a zone corresponding to the supply unit 111 (heated by the supply unit-heating portion 131) and a zone corresponding to the collecting unit 115 (heated by the collecting unit-heating portion 135). The zone corresponding to the supply unit 111 (closest to the driving device 150) may have the highest temperature.

In addition, the collecting unit 115 of the inner tube 110 may be divided into a plurality of zones to be heated by the collecting unit-heating portion 135. The collecting unit-heating portion 135 may include a plurality of collecting unit-heating portions 135a, 135b, 135c, 135d that are arranged in a longitudinal direction of the collecting unit 115 and that independently control the temperature of the collecting units 115.

For example, a zone corresponding to the first collecting unit 115a may be heated by first collecting unit-heating portions 135a, 135b, a zone corresponding to the second collecting unit 115b may be heated by second collecting unit-heating portion 135c, and a zone corresponding to the third collecting unit 115c may be heated by a third collecting unit-heating portion 135d. For example, the temperatures of the collecting units 115 may be independently controlled.

Accordingly, the collecting unit 115 may be heated by the collecting unit-heating portion 135 in a state of being divided into a plurality of zones from the driving device 150 to the evacuator 140, in which a zone closest to the driving device 150, e.g., the zone corresponding to the first collecting unit 115a, may be heated to the highest temperature.

In an implementation, the inner tube 110 may be heated by dividing the supply unit 111 into a plurality of zones, or by dividing both the supply unit 111 and the collecting unit 115 into a plurality of zones. For example, the heater 130 may heat the inner tube 110 such that a zone closest to the driving device 150 may have the highest temperature.

With this heating structure for the inner tube 110, the purification target material may be sublimated or evaporated in the supply unit 111, and the purification target material may be sublimated or liquefied in the collecting unit 115 (in which materials having different properties, e.g., including different amounts of foreign matter or impurities, are sublimated or liquefied) to be respectively collected in the plurality of zones formed by dividing the collecting unit 115.

The evacuator 140 may evacuate the inner tube 110 into or using a vacuum. The evacuator 140 may be at the other side of the outer tube 120 (relative to the driving device 150) and may evacuate the outer tube 120 (which receives the inner tube 110 therein) thereby providing a minute pressure gradient in the respective zones of the inner tube 110.

As the inner tube 110 is evacuated by the evacuator 140, the purification target material on sides of the inner tube 110 may be sublimated or evaporated in a vacuum at a temperature that is lower than the temperature at which the purification target material would be sublimated or evaporated at atmospheric pressure. Further, in the supply unit 111, the sublimated or evaporated purification target material may move according to the pressure gradient caused by operation of the evacuator 140, and may be re-sublimated or liquefied to be collected in the collecting unit 115.

The driving device 150 may drive the inner tube 110. The driving device 150 may include a drive unit 151 and a power transmission unit 155.

The drive unit 151 may generate power for operating the inner tube 110. For example, the drive unit 151 may generate torque for rotating the inner tube 110.

The power transmission unit 155 may transmit the power (e.g., torque or rotational motion) generated by the drive unit 151 to the supply unit 111 to move the supply unit 111. For example, the power transmission unit 155 may transmit the torque for rotating the supply unit 111 to the supply unit 111. The power transmission unit 155 may include a power transmission member 156 and a supply unit-holding member 157.

The power transmission member 156 may connect the drive unit 151 to the supply unit-holding member 157 such that power may be transmitted from the drive unit 151 to the supply unit-holding member 157. For example, the power transmission member 156 may be rotated by the drive unit 151 and thus may rotate the supply unit-holding member 157.

Referring to FIGS. 1 to 3, the supply unit-holding member 157 may receive power (in cooperation with the power transmission member 156), and may transmit the power to the supply unit 111. For example, the supply unit-holding member 157 may be rotated in cooperation with the power transmission member 156, and may rotate the supply unit 111. The supply unit-holding member 157 may include an outward holding portion 157a and a longitudinal holding portion 157b.

The outward holding portion 157a may extend to surround an outer surface of the supply unit 111. For example, the outward holding portion 157a may extend to surround the outer surface of the supply unit 111 in a circumferential direction thereof, and may include a plurality of outward holding portions separated from each other and arranged in or along the longitudinal direction of the supply unit 111.

The longitudinal holding portion 157b may extend in the longitudinal direction of the supply unit 111, and may intersect the outward holding portion 157a. The longitudinal holding portion 157b may include a plurality of longitudinal holding portions separated from each other and arranged in or around the circumferential direction of the supply unit 111, and may intersect the outward holding portion 157a.

The apparatus 100 according to the present embodiment may further include, e.g., a mounting portion 150a, a pressing portion 150b, and a resilient portion 150c, as shown in FIGS. 3 to 5.

In an implementation, the supply unit-holding member 157 may be separated from the supply unit 111. The mounting portion 150a may pass through at least one of the outward holding portion 157a and the longitudinal holding portion 157b of the supply unit-holding member 157. In an implementation, the mounting portion 150a may be penetratingly formed at an intersection between the outward holding portion 157a and the longitudinal holding portion 157b. For example, the mounting portion 150 may penetrate the supply unit-holding member 157 at intersections between the outward holding portion 157a and the longitudinal holding portion 157b.

The pressing portion 150b may be placed on or in the mounting portion 150a, and may support the supply unit 111. In an implementation, the pressing portion 150b may be formed in a shape, e.g., a spherical shape. The pressing portion 150b may be formed in a through-hole of the mounting portion 150a, and may be movable in a direction of approaching or moving away from the supply unit 111, such that the pressing portion 150b may contact or press the supply unit 111 and may support the supply unit 111 on the supply unit-holding member 157 in a state of being separated from the supply unit-holding member 157. For example, the pressing portion 150b may help maintain a separated state of the supply unit-holding member 157 and the supply unit 111.

The resilient portion 150c may press the pressing portion 150b toward the supply unit 111. In an implementation, the resilient portion 150c may be adjacent to the mounting portion 150a, and may be provided in the form of a leaf spring. For example, the resilient portion 150c may be secured at one side thereof to the supply unit-holding member 157 and another side thereof may contact the pressing portion 150b and may elastically press the pressing portion 150b toward the supply unit 111. The resilient portion 150c may elastically press the pressing portion 150b toward the supply unit 111 such that the pressing portion 150b may support the supply unit 111 in a state of being separated from the supply unit-holding member 157. For example, the resilient portion 150c may be elastically biased toward the supply unit 111 in order to press the pressing portion 150b toward the supply unit 111 to help maintain the separation of the supply unit 111 from the supply unit-holding member 157.

As described above, an assembly of the pressing portion 150b (movably placed on the mounting portion 150a) and the resilient portion 150c (elastically pressing the pressing portion 150b toward the supply unit 111) may not only serve as a coupling medium for detachably coupling the supply unit 111 and the power transmission unit 155 (see FIG. 1), but may also allow the supply unit 111 and the power transmission unit 155 (formed of different materials and having different coefficients of thermal expansion) to be coupled to each other without contact, e.g., without directly contacting one another.

Such an assembly of the pressing portion 150b and the resilient portion 150c may be changed in shape corresponding to a change in shape due to thermal expansion of the supply unit 111 or the power transmission unit 155. Thus coupling between the supply unit 111 and the power transmission unit 155 may be stably maintained, even in the case where the supply unit 111 and the power transmission unit 155 (heated together with the purification target material to be sublimated or evaporated) are different in degree of thermal expansion.

For example, when the supply unit 111 is formed of quartz, and the power transmission unit 155 is formed of metal (such as stainless steel), even if the power transmission unit 155 (formed of a material having a relatively high coefficient of thermal expansion) were to expand to a greater degree than the supply unit 111, and a gap were to be formed between the supply unit 111 and the power transmission unit 155, the coupling portion between the supply unit 111 and the power transmission unit 155 may be stably supported by the assembly of the pressing portion 150b and the resilient portion 150c. Accordingly, the supply unit 111 may be stably rotated without being shaken.

Further, in the apparatus 100 according to the present embodiment and as shown in FIG. 1, the supply unit 111 may be detachably coupled with the power transmission unit 155. In addition, the assembly of the inner tube 110 and the driving device 150 may be detachably coupled with the outer tube 120.

Thus, the supply unit 111 may be easily repaired or replaced by detaching the supply unit 111 from the power transmission unit 155. In an implementation, the purification target material may be supplied to the supply unit 111 after separating the inner tube 110 from the outer tube 120.

The coupling portion or coupling structure between the driving device 150 and the outer tube 120 may include a sealing portion 159. The sealing portion 159 may seal the coupling portion between the driving device 150 and the outer tube 120 to seal the outer tube 120, thereby maintaining the outer tube 120 and the inner tube 110 in a vacuum.

Figure 6:
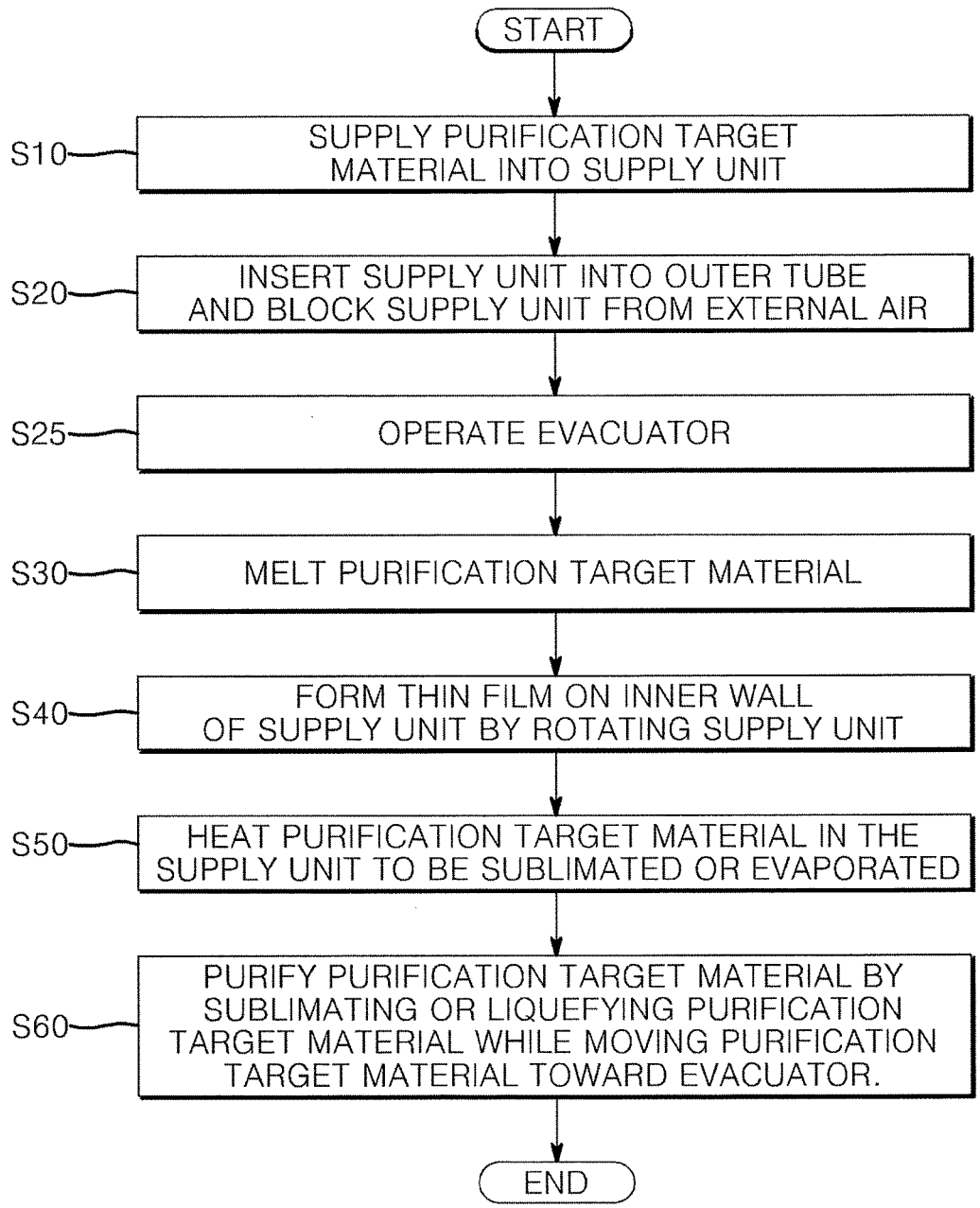
FIG. 6 illustrates a flowchart of a method for purifying an organic compound in accordance with the first embodiment.

FIG. 6 illustrates a flowchart of a method of purifying an organic compound using the apparatus in accordance with the first embodiment.

Hereinafter, operation and effects of the apparatus and method for purifying an organic compound in accordance with the first embodiment will be described with reference to FIGS. 1 to 6.

Referring to FIGS. 1 to 6, in order to purify a purification target material using the apparatus 100 according to an embodiment, the purification target material (e.g., potentially including impurities) may first be supplied into the supply unit 111 (S10). Supplying the purification target material into the supply unit 111 may be achieved by directly placing the purification target material into the supply unit 111 (e.g., after the assembly of the supply unit 111 and the driving device 150 are removed from the outer tube 120), or by providing the purification target material to the deposition portion 113 via the discharge port 112 (e.g., after the supply unit 111 is separated from the supply unit-holding member 157). In an implementation, the purification target material may be, e.g., a material for an electron transport layer (ETL).

As described above, when the supply unit 111 receives the purification target material, the supply unit 111 may be inserted into and coupled with the supply unit-holding member 157 and inserted into the outer tube 120. Then, the sealing portion 159 may block the supply unit 111 from external air (S20), e.g., may seal the supply unit 111. In this state, the evacuator 140 may be operated to evacuate the inner tube 110 into a vacuum while forming a minute pressure gradient in respective sections of the inner tube 110 (S25).

Then, the heater 130 may be operated to melt the purification target material in the supply unit 111 (S30). In an implementation, the purification target material supplied to the supply unit 111, e.g., to the deposition portion 113, may be heated and melted in the deposition portion 113 as the supply unit 111 is heated by the supply unit-heating portion 131 (which may be at a side of the supply unit 111).

In an implementation, in the heater 130, only the supply unit-heating portion 131 may be operated to thus heat only the zone corresponding to the supply unit 111. In an implementation, both the supply unit-heating portion 131 and the collecting unit-heating portion 135 may be operated to heat both the supply unit 111 and the collecting unit 115.

As described above, when the purification target material is partially or completely melted, the supply unit 111 may be rotated such that a thin film p may be formed on the inner wall of the supply unit 111, e.g., on the inner wall of the deposition portion 113 (S40). In an implementation, the supply unit 111 may be rotated by operation of the driving device 150. For example, the purification target material F (melted in the deposition portion 113) may be deposited as a thin film p on the inner wall of the deposition portion 113 while sequentially contacting the inner wall of the deposition portion 113 in a direction of rotating the supply unit 111 upon rotation of the supply unit 111.

In an implementation, the discharge port 112 may have the greater height than the deposition portion 113 (e.g., may have a smaller diameter than that of the deposition portion 113), and the purification target material F (stored and melted in the deposition portion 113) may not flow toward an outside of the supply unit 111 during rotation of the supply unit 111.

In an implementation, the supply unit 111 may be rotated after the purification target material is completely melted. In an implementation, the supply unit 111 may be rotated while the purification target material is partially melted, and various modifications may be made.

As the purification target material forms the thin film p on the inner wall of the deposition portion 113 (through rotation of the supply unit 111), the purification target material (supplied to the supply unit 111) may be heated to be sublimated or evaporated (S50).

The heating may be achieved by the heater 130, e.g., heating of the purification target material (in the supply unit 111) to be sublimated or evaporated may be achieved by the supply unit-heating portion 131. The supply unit-heating portion 131 may heat the supply unit 111 to a temperature equal to or higher than a sublimation point or evaporation point of the purification target material. Thus, the purification target material supplied to the supply unit 111 may be sublimated or evaporated.

The inner tube 110 may be evacuated under vacuum by the evacuator 140, and the purification target material may be sublimated or evaporated under a vacuum at a temperature lower than the temperature that the purification target material would be sublimated or evaporated at atmospheric pressure.

In an implementation, the driving device 150 may rotate the supply unit 111 in the state that the purification target material is melted in the deposition portion 113, and the purification target material may be deposited as a thin film over or on the inner wall of the deposition portion 113. The thin film of the purification target material (on the inner wall of the deposition portion 113) may enlarge the surface area of the purification target material to be sublimated or evaporated. Thus, the purification target material may be more quickly and efficiently sublimated or evaporated under the same temperature conditions. For example, impurities having a sublimation temperature or evaporation temperature that is higher than the temperature to which the deposition portion is heated may remain in solid or liquid form on inner walls or at the bottom of the deposition portion, and thus may not be transferred to the collecting unit 115.

The heating may be undertaken to allow the respective zones of the inner tube 110 to have different temperature gradients. Thus, the heater 130 may heat the zone of the inner tube 110 farthest away from the evacuator 140 (among the plurality of zones formed by dividing the inner tube 110) to have a temperature equal to or higher than the sublimation or evaporation point of the purification target material (e.g., but lower than potential impurities in the material), and may heat the other zones of the inner tube 110 to have a temperature lower than the sublimation or evaporation point thereof (e.g., but higher than other potential impurities in the material). For example, the temperature gradient may be such that the temperature of the inner tube 110 is gradually lowered from the zone of the inner tube 110 that is farthest from the evacuator 140 to the zone of the inner tube 110 that is closest to the evacuator 140.

For example, the supply unit 111 may be heated by the supply unit-heating portion 131 to a temperature equal to or higher than the sublimation or evaporation point of the purification target material, and the collecting unit 115 may be heated by the collecting unit-heating portion 135 to a temperature lower than the sublimation or evaporation point of the purification target material. For example, the evaporated or sublimated material from the supply unit 111 may condense in the collecting unit 115 to be collected and purified. For example, the temperature gradient may be such that that the temperature of the collecting unit 115 is gradually lowered from the zone of the collecting unit 115 that is farthest from the evacuator 140 to the zone of the collecting unit 115 that is closest to the evacuator 140.

In an implementation, the foregoing heating operation may be achieved by first heating the supply unit 111 and then heating the collecting unit 115 with a time lag therebetween, or by simultaneously heating both the supply unit 111 and the collecting unit 115.

When the purification target material is heated as above to thus be sublimated or evaporated, the purification target material may be sublimated or liquefied for purification while moving the purification target material toward the evacuator 140 (S60).

In an implementation, movement of the sublimated or evaporated purification target material in the supply unit 111 may be achieved along a minute pressure gradient formed in the inner tube 110 by operation of the evacuator 140. While the purification target material moves along the pressure gradient, the purification target material may be sublimated or liquefied in each corresponding zone of the collecting unit 115 (that is heated to a temperature range of a sublimation or evaporation point of a target product).

For example, a material having the highest purity may be collected in a zone of the first collecting unit 115a (that is heated to have the highest temperature within a temperature range lower than the sublimation or evaporation point of the purification target material). A material having the same or lower purity as that in the first collecting unit 115a, or containing more foreign matter, may be collected in a zone of the second collecting unit 115b (that is heated to have a temperature gradually lower than that of the first collecting unit 115a). Foreign matter may be collected in a zone of the third collecting unit 115c (that is heated to have a temperature lower than that of the second collecting unit 115b).

For example, an initial purification target material may include the desired organic compound along with impurities or foreign matter. The purification target material may be supplied to the supply unit 111. The purification target material may be rotated and heated in the deposition portion 113 of the supply unit to be melted and then sublimated or evaporated, leaving some of the impurities behind in solid or liquid form on inner walls or at the bottom of the deposition portion 113. The volatile, evaporated or sublimated purification target material (including the desired organic compound) may move through the discharge port into the collecting unit 115. The temperature in the collecting unit 115 may be lower than the sublimation or evaporation temperature of the desired organic compound and/or the purification target material, and the organic compound and/or the purification target material may condense in the collecting unit. Then, the organic compound and/or the purification target material in the collecting unit may be heated at a temperature that is greater than an evaporation or sublimation temperature of impurities therein, but lower than the evaporation or sublimation temperature of the desired organic material. Accordingly, the impurities may be volatilized to be moved toward and removed by the evacuator, thereby leaving the purified organic compound to be collected in the collecting unit 115.

With the apparatus for purifying an organic compound in accordance with the first embodiment and the method using the same, an experiment of purifying a material for an electron transport layer (ETL) used in manufacture of an organic electroluminescent device was performed.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Experimental Example 1

592 g of a material for an ETL (tris(8-hydroxyquinoline) aluminum ($Alq_3$)) was supplied (as a purification target material) into the supply unit 111 of the inner tube 110, and the supply unit 111 was inserted into and coupled to the supply unit-holding member 157 such that the supply unit 111 was placed in a zone to be heated by the supply unit-heating portion 131. The supply unit 111 was inserted into the outer tube 120, and then the sealing portion 159 was used to block the supply unit 111 from external air.

Thereafter, the evacuator 140 was operated to evacuate the inner tube 110 into a vacuum, and the heater 130 was then operated to heat the purification target material in the inner tube 110.

The supply unit-heating portion 131 was heated to 300° C., which is higher than a melting point of the material for the ETL. The first collecting unit-heating portions 135a, 135b (of the collecting unit-heating portion 135) were heated to 290° C.; the second collecting unit-heating portion 135c was heated to 270° C.; the third collecting unit-heating portion 135d was heated to 180° C. The driving device 150 was operated to rotate the supply unit 111 at a time point when most of the purification target material was melted into a liquid state.

After 3 hours from the beginning point of the experiment, the temperature of the heater 130 was adjusted to start purification. To this end, the supply unit-heating portion 131 was heated to 325° C.; the first collecting unit-heating portions 135a, 135b were heated to 320° C., the second collecting unit-heating portion 135c was heated to 260° C., and the third collecting unit-heating portion 135d was heated to 150° C. The temperature of 325° C. for heating the supply unit-heating portion 131 was sufficient to evaporate the purification target material.

For comparison with another purification method, the materials remaining in the supply unit 111 and the collecting unit 115 upon completion of purification were collected, and time taken for purification, the weight of the purification target material remaining in the supply unit 111, and purity of the material collected in the collecting unit 115 were measured.

Experimental Example 2 and Experimental Example 3

Experimental example 2 and Experimental Example 3 were performed by repeating the procedure of Experimental Example 1 to increase reliability of the experiment, and were performed in the same manner as in Experimental Example 1 except for the amount of the purification target material supplied to the supply unit 111.

Specifically, the amount of the purification target material in Experimental Example 1 was 592 g, while those of Experimental Examples 2 and 3 were 500 g and 513 g, respectively.

For comparison of the purified materials obtained from the experiments, the materials were collected and processed by the same method as that of Experimental Example 1.

Comparative Example

For comparison with the foregoing experiments, an experiment based on another purification method was performed as follows.

After the supply unit 111, the driving device 150, and the sealing portion 159 used in Experimental Examples 1, 2, and 3 were removed, a separate supply unit 111 (configured not to move and rotate and receiving a purification target material) was connected to the collecting unit 115 within the outer tube 120.

500 g of a material for an ETL was supplied as a purification target material into the supply unit 111, and the evacuator 140 was operated to evacuate the supply unit 111 into a vacuum. Then, the heater 130 was operated to heat the purification target material in the supply unit 111.

The supply unit-heating portion 131 was heated to 300° C., which is higher than a melting point of the material for the ETL; the first collecting unit-heating portions 135a, 135b (of the collecting unit-heating portion 135) were heated to 290° C.; the second collecting unit-heating portion 135c was heated to 270° C.; the third collecting unit-heating portion 135d was heated to 180° C., thereby completely melting the purification target material into a liquid state.

After 3 hours from the beginning point of the experiment, the temperature of the heater 130 was adjusted to start purification. Specifically, the supply unit-heating portion 131 was heated to 325° C.; the first collecting unit-heating portions 135a, 135b were heated to 320° C., the second collecting unit-heating portion 135c was heated to 260° C., and the third collecting unit-heating portion 135d was heated to 150° C. The temperature of 325° C. for heating the supply unit-heating portion 131 was sufficient to evaporate the purification target material.

In order to compare the foregoing Experimental Examples 1, 2 and 3 with this Comparative Example, the materials remaining in the supply unit 111 and the collecting unit 115 upon completion of purification were collected, and time taken for purification, the weight of the purification target material remaining in the supply unit 111, and purity of the material collected in the collecting unit 115 were measured.

Results are as shown in the following Table 1.

TABLE 1

|  | Amount | Time taken for purification | Amount remaining in supply unit | Purifying speed | Speed ratio | Purity | Yield |
| --- | --- | --- | --- | --- | --- | --- | --- |
| Comparative Example | 500 g | 13.0 hr | 73.5 g | 32.8 g/hr | — | 99.97% | 85.30% |
| Experimental Example 1 | 592 g | 5.6 hr | 37.0 g | 99.1 g/hr | 3.0 times | 99.98% | 93.75% |
| Experimental Example 2 | 500 g | 4.0 hr | 32.0 g | 117.0 g/hr | 3.5 times | 99.98% | 93.60% |
| Experimental Example 3 | 513 g | 4.3 hr | 33.7 g | 111.5 g/hr | 3.4 times | 99.97% | 93.43% |

Purifying speed=[Amount of purification target material supplied to supply unit (g)−remaining amount in supply unit (g)]/Purifying time (hr)

Referring to Table 1, it may be seen that the purified materials prepared in all of Experimental Examples 1, 2, and 3 had higher purity, three or more times faster purifying speeds, and higher yield than the Comparative Example.

Based on the results shown in Table 1, it may be determined that the material having high purity may be obtained at high speed and in high yield through the apparatus and method for purifying an organic compound in accordance with the first embodiment.

As described above, in the apparatus and method for purifying an organic compound in accordance with the first embodiment, the driving device 150 may rotate the supply unit 111 such that the purification target material may be deposited as a thin film throughout the inner wall of the deposition portion 113, thereby enlarging the surface area on which the purification target material is sublimated or evaporated, while increasing heat transfer efficiency for the purification target material.

In the apparatus and method for purifying an organic compound in accordance with the first embodiment, the purification target material may be more quickly and efficiently sublimated or evaporated under the same temperature conditions, and the purifying speed may be increased such that the purification target material may be purified in a more amount per hour under stable conditions than another purification method, thereby improving purity and yield.

In addition, in the apparatus and method for purifying an organic compound according to an embodiment, the supply unit 111 and the power transmission unit 155 may be coupled to each other without contact, e.g., direct contact, and the supply unit 111 and the power transmission unit 155 may be stably coupled regardless of thermal expansion, even though the supply unit 111 and the power transmission unit 155 may differ in degree of thermal expansion, thereby preventing shaking during rotation of the supply unit 111.

Figure 7:
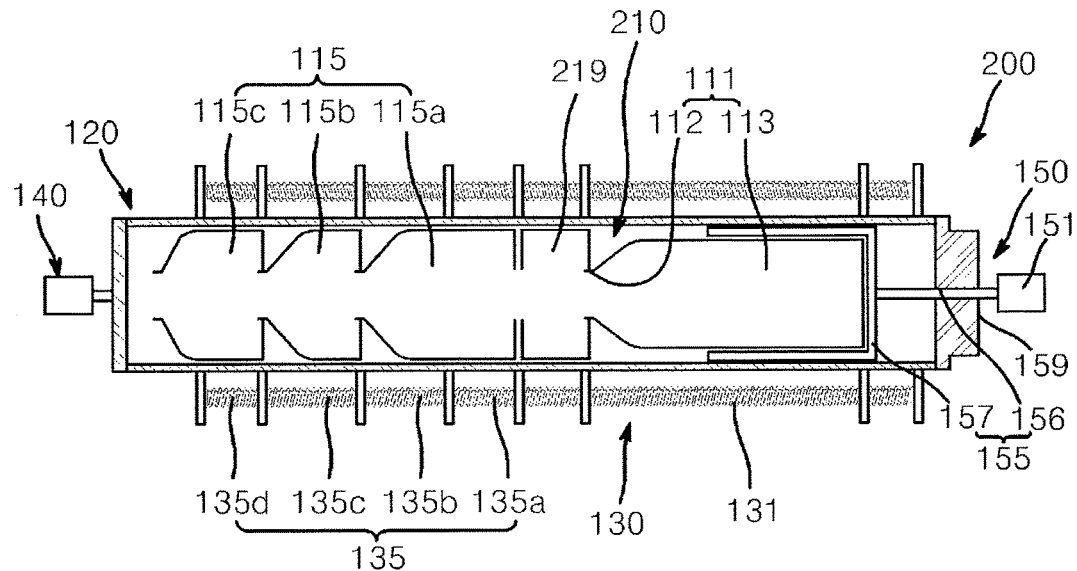
FIG. 7 illustrates a schematic view of an apparatus for purifying an organic compound in accordance with a second embodiment.
Figure 8:
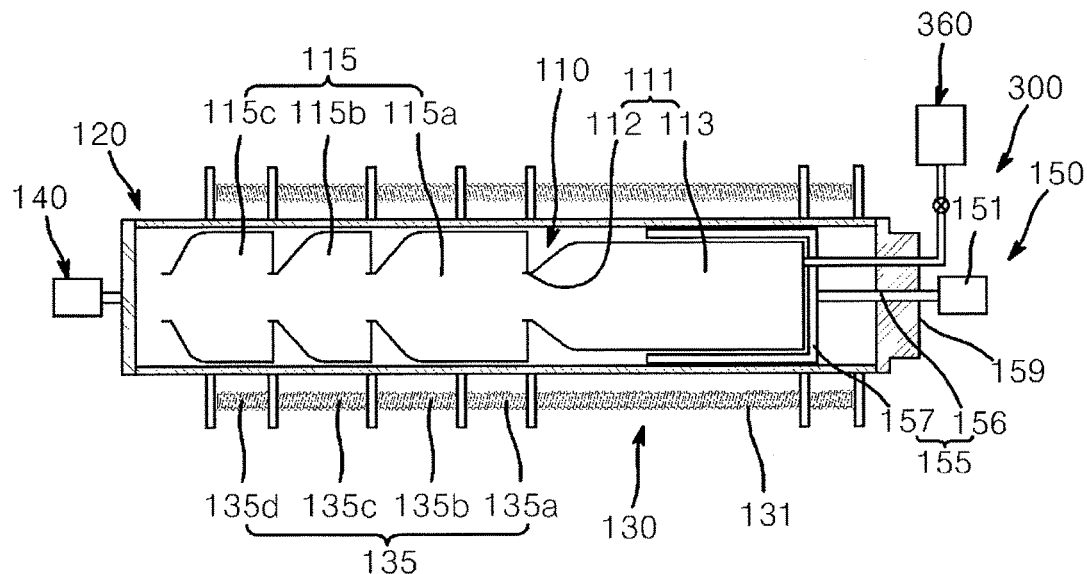
FIG. 8 illustrates a schematic view of an apparatus for purifying an organic compound in accordance with a third embodiment.
Figure 9:
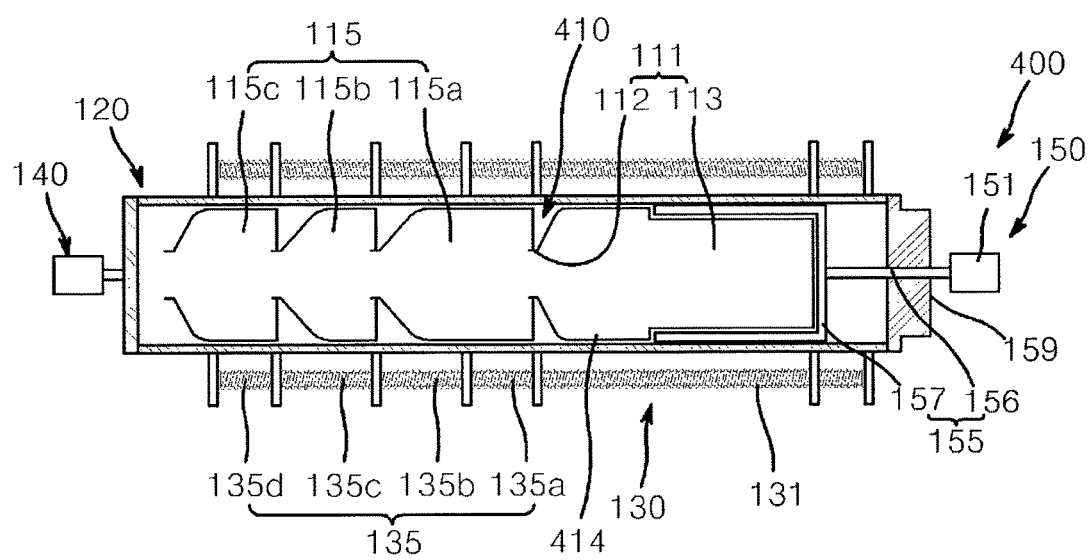
FIG. 9 illustrates a schematic view of an apparatus for purifying an organic compound in accordance with a fourth embodiment.

FIG. 7 illustrates a schematic view of an apparatus for purifying an organic compound according to a second embodiment, FIG. 8 illustrates a schematic view of an apparatus for purifying an organic compound according to a third embodiment, and FIG. 9 illustrates a schematic view of an apparatus for purifying an organic compound according to a fourth embodiment.

Next, the apparatus for purifying an organic compound according to second to fourth embodiments will be described with reference to FIGS. 7 to 9. Here, like reference numerals refer to like elements having the same functions throughout the drawings, and thus repeated descriptions thereof may be omitted.

Referring to FIG. 7, according to the second embodiment, an apparatus 200 for purifying an organic compound may further include a buffer 219 in an inner tube 210. The buffer 219 may be between a supply unit 111 and a collecting unit 115. The buffer 219 may collect foreign matter from a purification target material that has been sublimated or evaporated in the supply unit 111. According to this embodiment, a foreign substance or matter having a high molecular weight (among the foreign matter of the purification target material) may fall and may be collected in the buffer 219.

Referring to FIG. 8, according to the third embodiment, an apparatus 300 for purifying an organic compound may further include a carrying gas supplier 360. The carrying gas supplier 360 may supply a carrying gas for moving the sublimated or evaporated purification target material to the evacuator 140.

Nitrogen gas (or similar inert gas) may be used as the carrying gas. The carrying gas supplier 360 may supply the carrying gas to be moved from the driving device 150 toward the evacuator 140, thereby generating a flow for guiding the sublimated or evaporated purification target material toward the evacuator 140.

In the apparatus 300 for purifying an organic compound according to the third embodiment (which includes the carrying gas supplier 360), the temperature in respective zones of the heater 130 and the flux of the carrying gas may be controlled to adjust a location in which the purification target material will be collected in the collecting unit 115.

Referring to FIG. 9, according to the fourth embodiment, an apparatus 400 for purifying an organic compound may further include a surface-area enlarging portion 414 in an inner tube 410. In this embodiment, the surface-area enlarging portion 414 may be convexly expanded from the supply unit 111.

The surface-area enlarging portion 414 may help improve heating efficiency for the purification target material by enlarging a surface area inside the inner tube 410, e.g., an inner surface area of the supply unit 111. For example, the surface area-enlarging portion 414 may include a structure that increases an overall surface area of the inner wall of the deposition portion 113. Thus, a heating area for the purification target material supplied to the supply unit 111 (e.g., the deposition portion 113) may be enlarged.

In an implementation, the supply unit 111 (having the surface-area enlarging portion 414) may help increase the difference in height between the discharge port 112 and the deposition portion 113 (e.g., a difference in diameters between the discharge port 112 and the deposition portion 113 may be increased). For example, the purification target material (that is stored and melted in the deposition portion 113) may be effectively prevented from running to an outside of the supply unit 111 during rotation of the supply unit 111.

By way of summation and review, an organic compound used for an organic electroluminescent device may be purified. For example, a technique for purification of the organic compound may separate only a pure pigment component from the organic compound to use the pigment component for thin film deposition. With the development of the technique for purification of the organic compound, color purity and luminous efficacy may be improved, and luminescence lifetime of the organic electroluminescent device may also be extended. For mass production of the organic compound, a purifying technique capable of improving speed, purity and yield may be desirable.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An apparatus for purifying an organic compound, the apparatus comprising:
   an inner tube that receives a purification target material therein;
   a heater that heats the purification target material received in the inner tube;
   an evacuator that evacuates the inner tube into a vacuum; and
   a driving device that drives the inner tube,
   wherein the inner tube includes:
      a supply unit to which the purification target material is supplied; and
      a collecting unit in which the purification target material is sublimated or liquefied as it moves toward the evacuator,
   wherein the driving device includes:
      a drive unit that generates power; and a power transmission unit that transmits the power generated by the drive unit to the supply unit to move the supply unit, wherein the power transmission unit includes:
- a power transmission member that receives power from the drive unit; and
- a supply unit-holding member that transmits power received in cooperation with the power transmission member to the supply unit, and wherein the supply unit-holding member includes:
- an outward holding portion that extends to surround an outer surface of the supply unit; and
- a longitudinal holding portion that extends in a longitudinal direction of the supply unit and intersects the outward holding portion.

2. The apparatus as claimed in claim 1, wherein at least one collecting unit is between the supply unit and the evacuator.

3. The apparatus as claimed in claim 1, further comprising a buffer between the supply unit and the collecting unit, the buffer collecting foreign matter from the purification target material that is sublimated or evaporated in the supply unit.

4. The apparatus as claimed in claim 1, wherein the supply unit includes:
- a deposition portion that stores the purification target material, the deposition portion having an inner wall on which the purification target material is deposited as a thin film, and
- a discharge port open toward the collecting unit, the discharge port being configured to discharge the sublimated or evaporated purification target material from the deposition portion toward the collecting unit;

wherein the discharge port is concentric with the deposition portion, the discharge port having a diameter smaller than a diameter of the deposition portion.

5. The apparatus as claimed in claim 1, wherein the power transmission unit rotates the supply unit.

6. The apparatus as claimed in claim 1, further comprising:
- a mounting portion on at least one of the outward holding portion and the longitudinal holding portion;
- a pressing portion on the mounting portion, the pressing portion supporting the supply unit; and
- a resilient portion that presses the pressing portion toward the supply unit.

7. The apparatus as claimed in claim 6, wherein:
- the supply unit-holding member is separated from the supply unit,
- the mounting portion includes a through hole penetrating the supply unit-holding member further, and
- the pressing portion contacts the supply unit.

8. The apparatus as claimed in claim 1, wherein the supply unit is detachably coupled with the power transmission unit.

9. The apparatus as claimed in claim 1, wherein the heater:
- heats the purification target material that is in the supply unit to be sublimated or evaporated, and
- heats the purification target material that is moving along the collecting unit to be sublimated or liquefied.

10. The apparatus as claimed in claim 1, wherein the heater includes:
- a supply unit-heating portion that heats the supply unit; and
- a collecting unit-heating portion that heats the collecting unit, the collecting unit-heating portion heating the collecting unit to a temperature that is lower than a temperature to which the supply unit-heating portion heats the supply unit.

11. The apparatus as claimed in claim 1, wherein:
- the inner tube is divided into a plurality of heating zones that are arranged from the driving device to the evacuator, and
- the heater heats the inner tube such that a zone closest to the driving device has a highest temperature.

12. The apparatus as claimed in claim 1, further comprising:
- an outer tube accommodating the inner tube, the driving device being at one side of the outer tube and at the evacuator being at another side of the outer tube; and
- a sealing portion that seals a coupling portion between the driving device and the outer tube to seal the outer tube.

13. The apparatus as claimed in claim 1, further comprising a carrying gas supplier that supplies a carrying gas, the carrying gas moving the sublimated or evaporated purification target material toward the evacuator.

14. The apparatus as claimed in claim 1, wherein the inner tube includes a surface-area enlarging portion that enlarges a surface area inside the inner tube.

15. The apparatus as claimed in claim 1, wherein the organic compound includes a material for an organic electroluminescent device.

16. A method of purifying an organic compound using the apparatus as claimed in claim 1, the method comprising:
- supplying the purification target material to the supply unit;
- melting the purification target material;
- rotating the supply unit to form a thin film of the purification target material on an inner wall of the supply unit;
- heating the purification target material in the supply unit to be sublimated or evaporated; and
- purifying the purification target material by sublimating or liquefying the purification target material while moving the purification target material toward the evacuator.

17. The method as claimed in claim 16, wherein supplying the purification target material includes inserting the supply unit into an outer tube and then blocking the supply unit from external air with a sealing portion.

18. The method as claimed in claim 16, wherein heating the purification target material includes heating the inner tube that is divided into a plurality of zones such that:
- a zone farthest away from the evacuator has a temperature equal to or higher than a sublimation or evaporation point of the purification target material, and
- other zones have a temperature lower than the sublimation or evaporation point of the purification target material.

19. The method as claimed in claim 18, wherein heating the purification target material includes heating the plurality of zones to have different temperatures such that a temperature gradient is formed along the inner tube.

20. The method as claimed in claim 16, wherein rotating the supply unit includes rotating the supply unit after completely melting the purification target material.

* * * * *